(12) United States Patent
Mohmand (10) Patent No.: US 9,814,479 B2
(45) Date of Patent: Nov. 14, 2017

(54) CARTILAGE HOLDING FORCEPS

(71) Applicant: Muhammad Farooq, Peshawar (PK)

(72) Inventor: Muhammad Humayun Mohmand, Islamabad (PK)

( * ) Notice: Subject to any disclaimer, the term of this patent is extended or adjusted under 35 U.S.C. 154(b) by 0 days.

(21) Appl. No.: 15/222,943

(22) Filed: Jul. 28, 2016

(65) Prior Publication Data

US 2016/0331391 A1    Nov. 17, 2016

(30) Foreign Application Priority Data

Jun. 7, 2016 (PK) ..................... 334/2016

(51) Int. Cl.
*A61B 17/30* (2006.01)
*A61B 17/28* (2006.01)
*A61B 17/04* (2006.01)

(52) U.S. Cl.
CPC ........ *A61B 17/282* (2013.01); *A61B 17/0483* (2013.01); *A61B 17/2833* (2013.01); *A61B 17/30* (2013.01); *A61B 2017/2837* (2013.01)

(58) Field of Classification Search
CPC ..... A61B 17/04; A61B 17/28; A61B 17/2812; A61B 17/0469; A61B 17/0483; A61B 17/062; A61B 2017/2926; A61B 10/06; A61B 17/282; B25B 9/02
USPC ....... 606/145, 148, 151, 157, 158, 205, 210, 606/211; 294/99.2
See application file for complete search history.

(56) References Cited

U.S. PATENT DOCUMENTS

| 671,337 A | * | 4/1901 | Gibson | A61B 17/0469 606/148 |
| 1,508,287 A | * | 9/1924 | Moran | D06F 59/08 294/99.2 |
| 2,665,692 A | * | 1/1954 | L Esperance | A61B 17/04 294/99.2 |
| 2,733,716 A | * | 2/1956 | Roberts | A44C 7/001 294/99.2 |
| 2,887,110 A | * | 5/1959 | Roeschmann | A61B 17/076 29/225 |
| 3,101,715 A | * | 8/1963 | Glassman | A61B 17/282 227/19 |
| 3,470,875 A | * | 10/1969 | Johnson | A61B 17/0469 606/145 |
| 3,815,607 A | * | 6/1974 | Chester | A61B 17/30 294/99.2 |
| 4,610,252 A | * | 9/1986 | Catalano | A61F 9/007 606/157 |

(Continued)

*Primary Examiner* — Kathleen Holwerda (57) ABSTRACT

This invention is an advanced tissue gripping forceps with novel design of forcep's jaw best suitable for medical surgery. The novel tissue holding forceps has first and second arms with two ends each i.e Head and rear end; and jaws at the heads of each arms of the forceps. The rear ends of two arms of the forceps are coupled together. The second ends, the head of the First and Second arms of the forceps form opposing First and second jaws which are resiliently biased apart. The First and second jaws each include a plurality of sharp, directly opposing sharp elongated teeth to grip the tissue firmly during the use. The both jaws has a deep "CUT" in the center which makes jaw as "U" shape. This novel design enable fast and easy surgical operations by reducing the time of operation by facilitating the stitching and other surgical operations.

10 Claims, 7 Drawing Sheets

(56) References Cited

U.S. PATENT DOCUMENTS

| | | | | |
|---|---|---|---|---|
| 4,843,753 | A | * | 7/1989 | Mace ..................... A01K 97/04 294/99.2 |
| 5,222,962 | A | * | 6/1993 | Burkhart ............ A61B 17/0469 606/139 |
| 5,257,637 | A | * | 11/1993 | El Gazayerli ...... A61B 17/0469 128/898 |
| 5,383,877 | A | * | 1/1995 | Clarke ............... A61B 17/0469 606/139 |
| 5,449,374 | A | * | 9/1995 | Dunn .................... A61B 17/02 294/99.2 |
| 5,997,567 | A | * | 12/1999 | Cangelosi .............. A61B 17/04 294/99.2 |
| 6,322,570 | B1 | * | 11/2001 | Matsutani .......... A61B 17/0469 606/139 |
| 8,608,774 | B1 | * | 12/2013 | Alshemari ............. A61B 17/30 606/210 |
| 2007/0083228 | A1 | * | 4/2007 | Visinoni ................ A61B 10/06 606/210 |

* cited by examiner

CARTILAGE HOLDING FORCEPS

TECHNICAL FIELD OF INVENTION

The present invention discloses a novel design of tissue holding forceps generally used in the medical surgery. Tissue forceps are used for grasping tissues during surgical operations which do not squeeze or crush soft tissue such as skin during use.

BACKGROUND ART

Tissue Forceps are devices used by doctors and medical practitioners to grip the soft tissue such as skin during surgery or other medical procedures. Traditionally, forceps have been available in a number of different type and designs like hemostatic forceps, tissue forceps, kelly forceps, and biopsy forceps. Conventional forceps have two grasping jaws at the top end thereof which can be plain or smooth, finely serrated so that they will not slip during grasping, or with interdigitating sharp elongated teeth. Such conventional forceps cause a considerable amount of crushing of tissues, leaving behind visible marks on the tissue.

The commonly known forceps design used by plastic surgeons is Adson-Brown forceps, with various modifications also. These forceps utilize opposing linear rows of fine teeth on each jaw of the forceps. In practice, such construction causes less trauma to tissue than the simple mouse tooth forceps or plain forceps with serrations.

However, conventional forceps have problems of slipping, crushing soft tissues; and do not have friendly design for easy and fast stitching during surgical operations. Accordingly, it is desired to provide an improved tissue forceps which not only avoid the crushing of tissue during use and support in stitching during surgery.

SUMMARY

The present disclosure is about novel design and techniques applied in the medical surgery. This invention is an advanced design of Adson-Brown forceps tissue gripping forceps with novel design of jaw which is best suitable for medical surgery. The novel tissue holding forceps has first and second arms with two ends each i.e Head end and Rear end; and jaws at the Head ends of each arms of the forceps. The rear ends of two arms of the forceps are coupled together. The second ends, the head ends of the First and Second arms of the forceps form opposing First and second jaws which are resiliently biased apart. The First and second jaws each include a plurality of sharp, directly opposing rows of linear sharp elongated teeth to grip the tissue firmly during its use. The both jaws has a deep linear "CUT" in the center which makes jaw as "U" shaped. This novel design enable fast and easy surgical operations by reducing the time of operation by facilitating the stitching and other surgical operations.

BRIEF DESCRIPTION OF THE DRAWINGS

The drawings are accompanied with this specification for the purpose of better disclosure of the present invention. These drawings are enclosed herewith and are a part of description. These illustrations made, along with the description help to explain the elements, features, structure and principles of the present disclosure as under:—

FIG. 01 is perspective view of present invention that is a Cartilage or Tissue Holding Forceps constructed and consistent with exemplary embodiments of the present disclosure.

FIG. 06 is perspective view of another shape present invention that is an electro-Cartilage or Tissue Holding Forceps constructed in accordance with exemplary embodiments of the present disclosure.

FIG. 07 is perspective view of another shape present invention that is a composite Cartilage or Tissue Holding Forceps constructed in accordance with exemplary embodiments of the present disclosure.

DETAILED DESCRIPTION

In the enclosed drawings exemplary scenario are described. These illustrations made, along with the description help to explain the elements, features, structure and principles of the present disclosure as under:—

Figure 01:
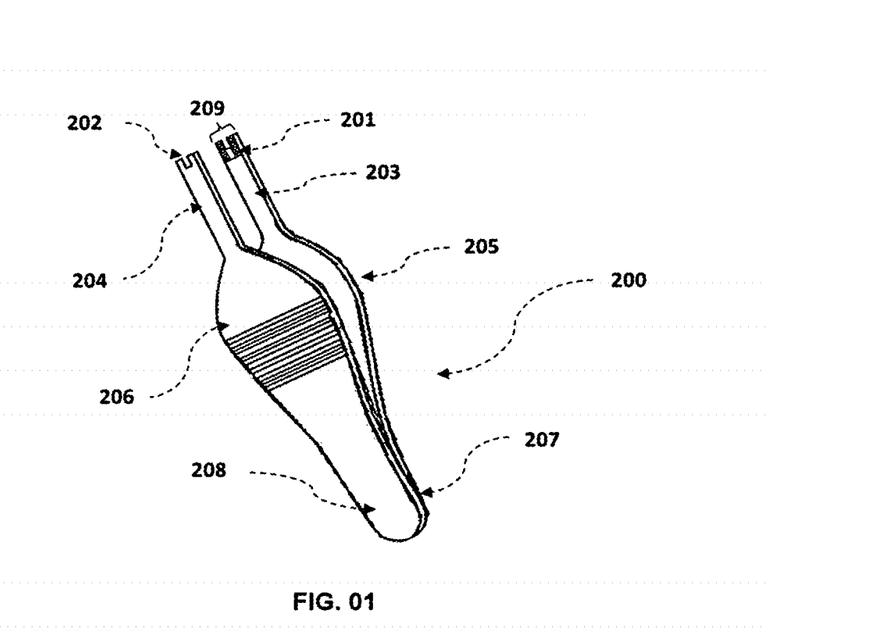

As depicted the perspective view of present invention in FIG. 01 that is a novel design of Cartilage or Tissue Holding Forceps constructed and consistent with exemplary embodiments of the present disclosure. The Tissue Holding Forceps (200) have first arm 205 and second arm 206 are coupled together with respective rear ends 207 and 208, respectively. The second ends of the arms, also represented as head ends 203 of the first arm 205 and 204 of the second arm 206, are open and opposing each other. 202 is the jaw at head end 204 and 201 is the jaw at head end 203 directly opposing each other. The 209 is jaw's tip which is cut in the center.

Figure 2A:
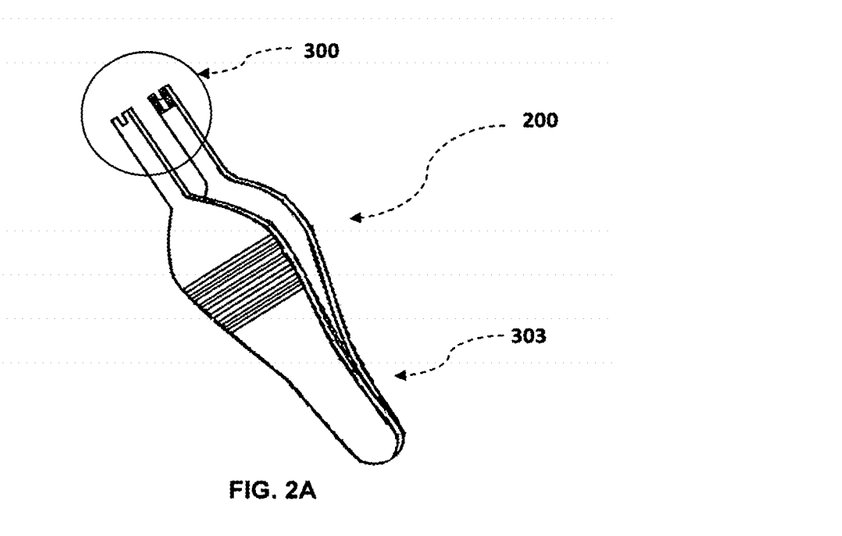
FIG. 2A is perspective view of present invention that is Cartilage or Tissue Holding Forceps and FIG. 2B is enlarged sectional view of jaw of Tissue Holding Forceps, consistent with exemplary embodiments of the present disclosure.
Figure 2B:
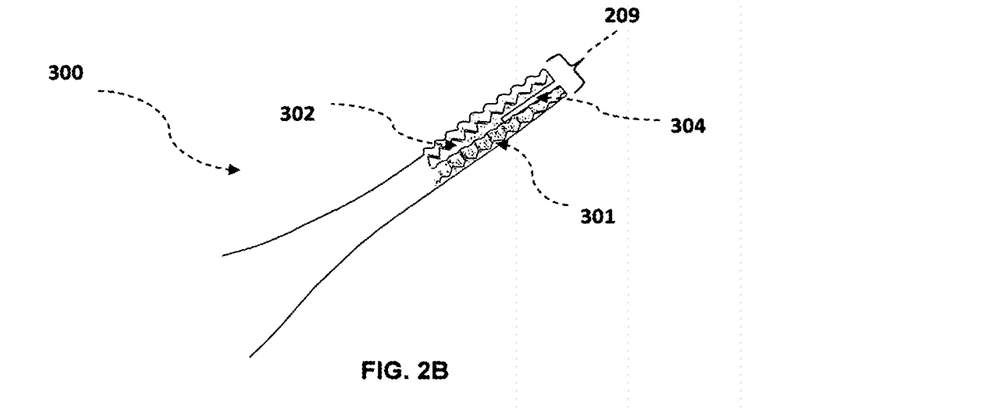

The perspective view of present invention shown in FIG. 2A is the novel design of Cartilage or Tissue Holding Forceps (200), consistent with exemplary embodiments of the present disclosure. The open end is encircled as 300 and coupled rear end is denoted as 303. As encircled in aforementioned FIG. 2A, the enlarged sectional view of open end is shown in FIG. 2B that is representing exemplary jaws (300) of the Tissue Holding Forceps (200), consistent with exemplary embodiments of the present disclosure. The jaw 300 has linear rows of triangle shaped sharp elongated teeth 301, a groove 302 in the center of the jaw and a deep linear cut 304. This makes the jaw's tip 209 as "U" shaped. The linear rows of the teeth 301 are also extended inside further even beyond the depth of cut 304.

Figure 3A:
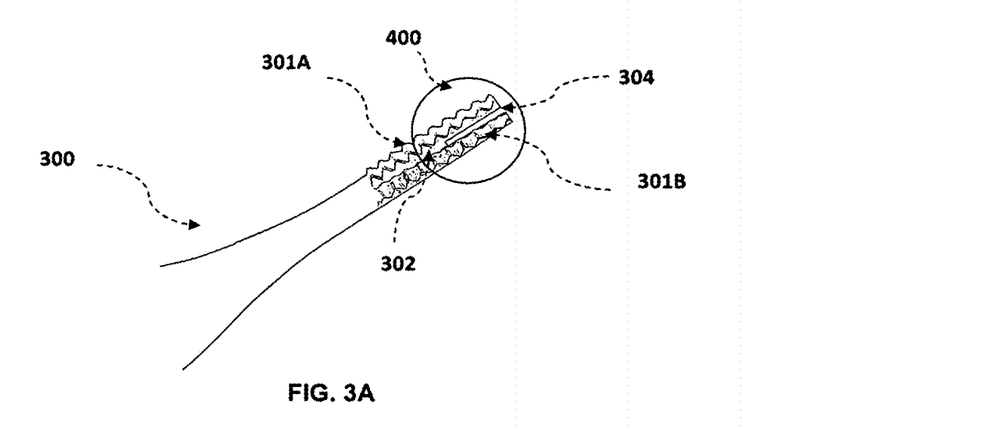
FIGS. 3A and 3B are enlarged sectional views of jaw of Tissue Holding Forceps, consistent with exemplary embodiments of the present disclosure.

The exemplary jaw 300 indicated in FIG. 3A has two linear rows of triangle shaped sharp elongated teeth 301A, and 301B on both sides of deep linear Cut 304. There is a deep groove 302 in the center of jaw and next to the deep linear Cut 304. This makes the jaw's tip 209 as "U" shaped. The linear rows of sharp elongated teeth 301 are also extended further even next to the depth of the Cut 304.

Figure 3B:
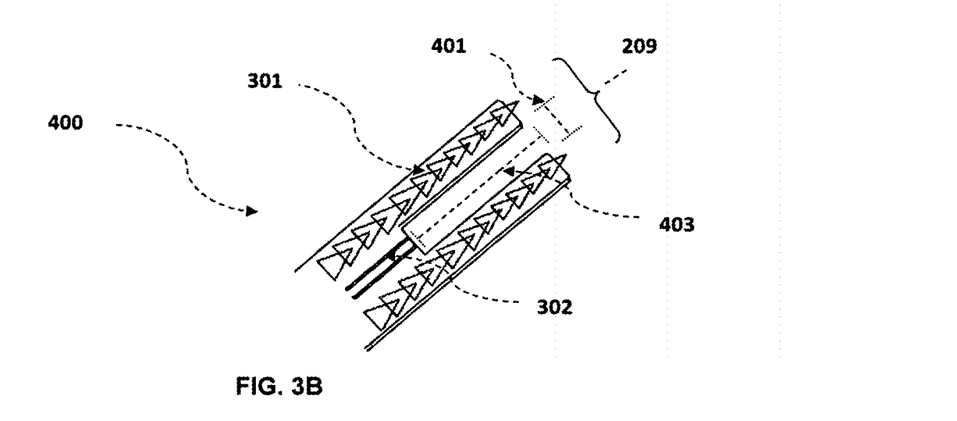

As encircled in above FIG. 3A, the enlarged sectional view 400 of the jaw's Tip 209 of Tissue Holding Forceps. The linear rows of sharp elongated teeth 301 and the deep groove 302 in the center of jaw are also shown here. The width of central cut 304 in the jaw's Tip 209 is indicated as 401 and linear depth of central cut is shown as 403.

Figure 4A:
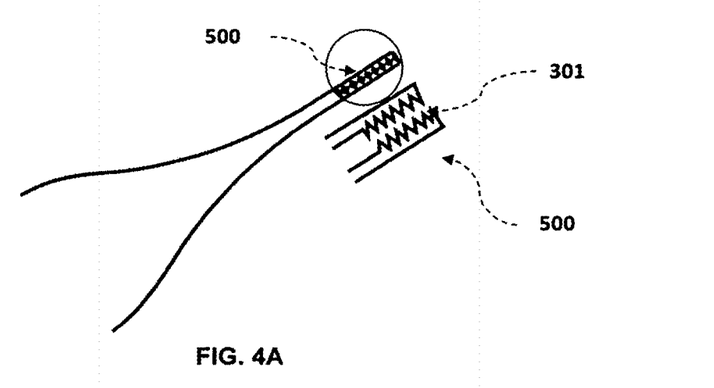
FIG. 4A is illustration of closed view of exemplary Cartilage or Tissue Holding Forceps and FIG. 4B-C is enlarged sectional view of open jaw of Tissue Holding Forceps, constructed in accordance with exemplary embodiments of the present disclosure.
Figure 4B:
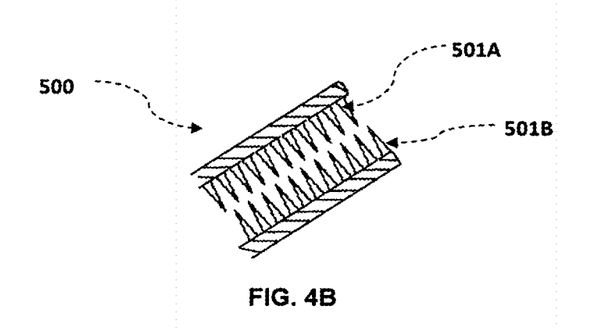
Figure 4C:
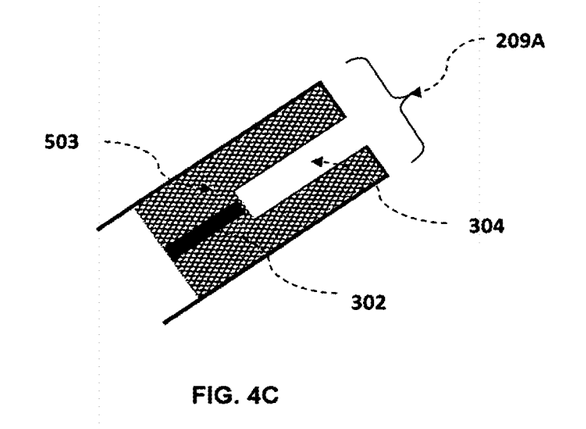

The sharp elongated teeth in linear rows (301A, 301B) of jaws are designed in such a manner that are adjusted at the closing of jaws of the open ends/head ends of first and second arm of the Cartilage or Tissue Holding Forceps. As shown in the FIG. 4A-4B where the enlarged illustration 500 of closed exemplary jaw is shown as 301 and arrangement of sharp elongated teeth at jaws of first arm 501A and at the jaws of second arm 501B of the exemplary Cartilage or Tissue Holding Forceps are shown as 500. The size and shape of the teeth at jaw may vary as per requirement. Teeth can be sharp elongated, sharp fine alike teeth of file and linear elongated sharp rows. A jaw with fine teeth are shown in the FIG. 4C where the novel design of Forceps' jaw with central cut 304 in the jaw's tip 209 is given with fine pyramidal shaped teeth 503 and central groove 302, constructed in accordance with exemplary embodiments of the present disclosure.

Figure 5A:
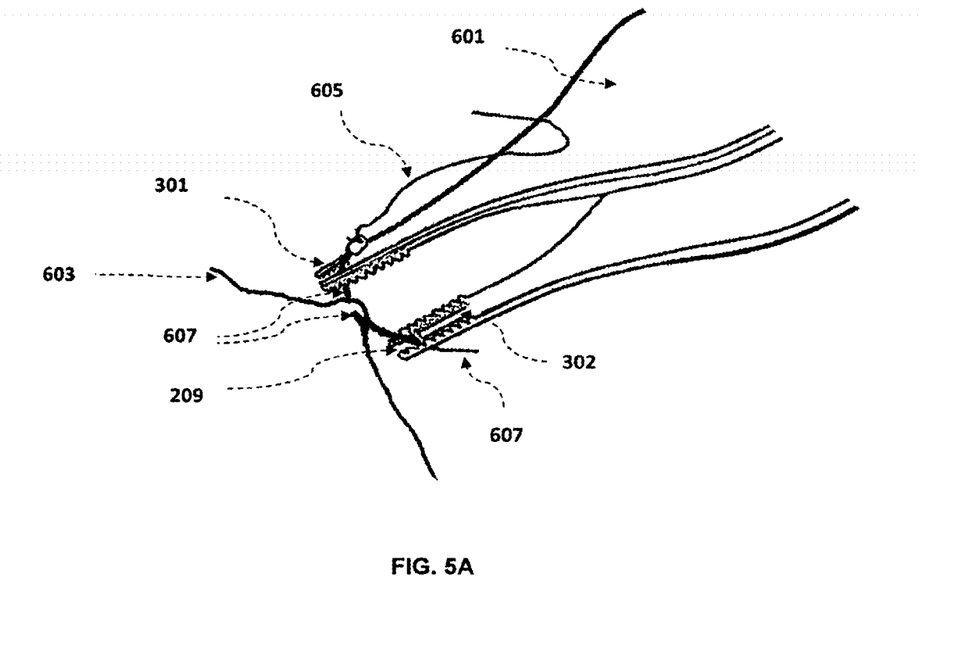
FIG. 5A is an illustration of a scenario of an exemplary application of present invention that is Cartilage or Tissue Holding Forceps during medical surgery, where the application of the novel forceps are consistent with exemplary embodiments of the present disclosure.
Figure 5B:
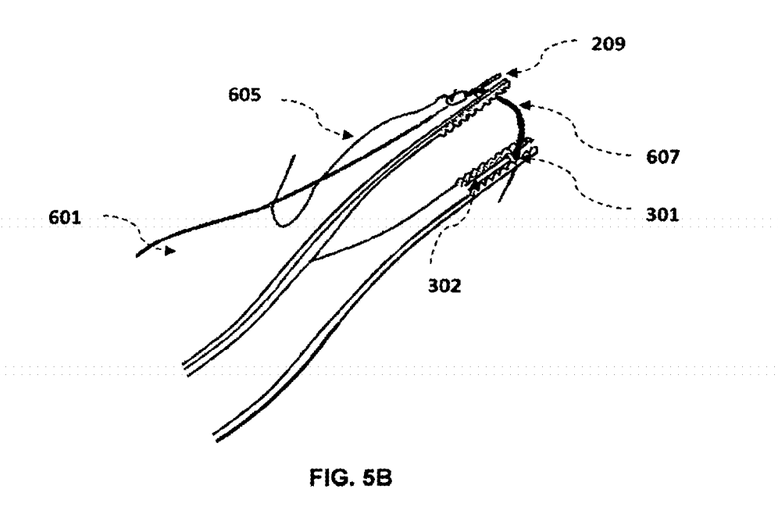
FIG. 5B is an enlarged sectional view of jaws of present invention that is Cartilage or Tissue Holding Forceps where the surgical needle is held by novel Forceps during medical surgery, where the application of the novel forceps are consistent with exemplary embodiments of the present disclosure.

This novel design with central cut in the jaw's tip 209 enable new and efficient use of tissue/cartilage gripping forceps. As an illustration is shown in FIG. 5A that is a scenario of an exemplary application of present invention 601 (i.e Cartilage or Tissue Holding Forceps) during medical surgery. In this exemplary medical surgical operation the stitching of cartilage/skin 603 is shown where surgical needle 607 is efficiently held by the novel designed forceps 601. The thread used for stitching is indicated as 605 and the required efficient grip of skin is achieved by means of right sized sharp elongated teeth 301 at jaws of the forceps. This is also further clearly shown in FIG. 6B which is an enlarged sectional view of jaws of Cartilage or Tissue Holding Forceps where the surgical needle 607 is held by novel Forceps 601 during medical surgery using thread 605, where the application of the novel forceps are consistent with exemplary embodiments of the present disclosure.

Figure 6:
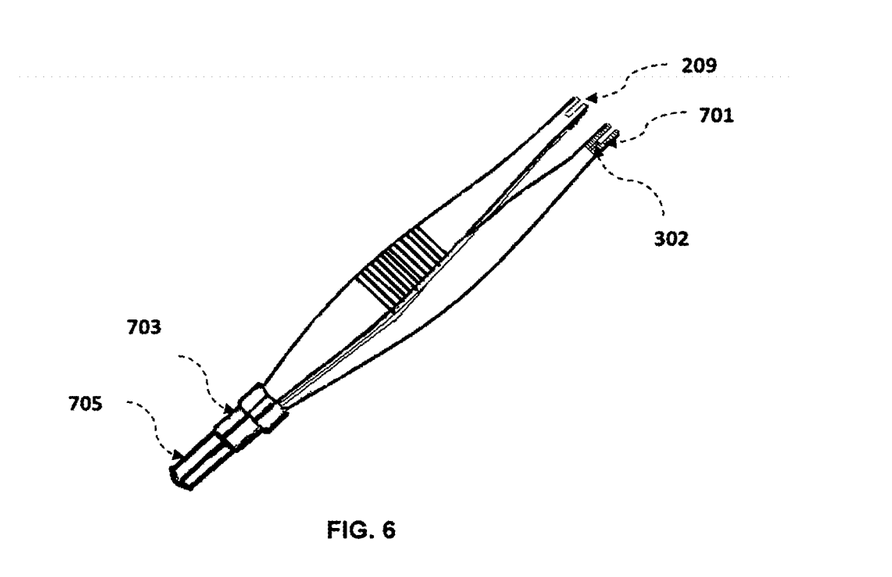

Another mode of present invention is shown in FIG. 06 which is a perspective view of that is an Electro-Cartilage or Tissue Holding Forceps (700) constructed in accordance with exemplary embodiments of the present disclosure. This electro-Tissue Holding Forceps are designed for procedures requiring critically precise temperature control to reduce sticking and charring while coagulating. The novel forceps 700 has novel designed jaw 701 with central cut jaw's tip 209, is connected with a holder 703 which is further connected to electric supply by electric wire 705.

Figure 7:
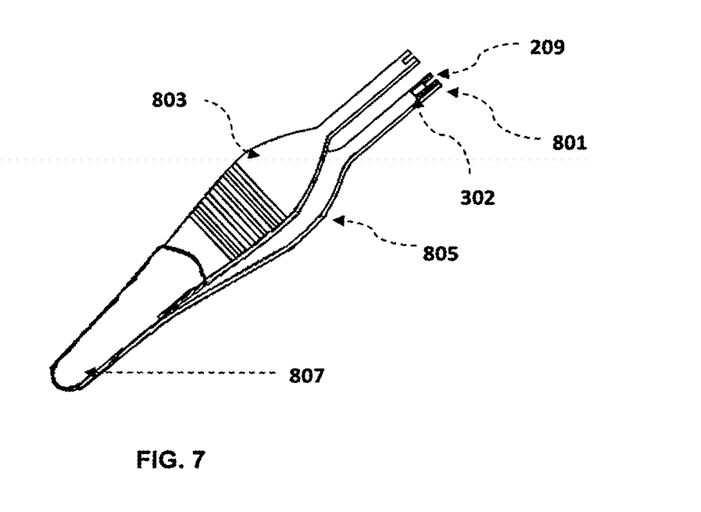

The replacement design for Adson Brown Tungsten Carbide Forceps with new technology is illustrated in FIG. 07 which is a perspective view of another mode of present invention (Cartilage or Tissue Holding Forceps) constructed in accordance with exemplary embodiments of the present disclosure. The novel forceps 800 has novel designed jaw 801 with central cut jaw's tip 209, where 803 and 805 are first and second arms of the novel designed forceps which are coupled together at point 807.

Figure 8A:
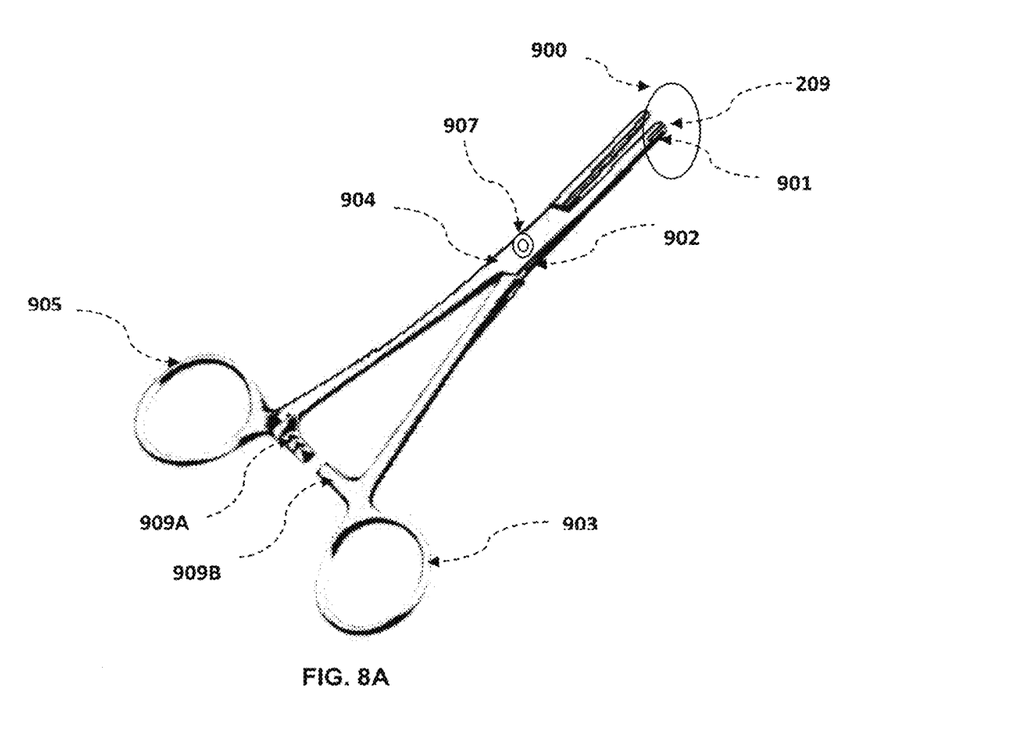
FIGS. 8A-B is perspective view of another shape present invention that is an adjustable gripping type Cartilage or Tissue Holding Forceps constructed in accordance with exemplary embodiments of the present disclosure.
Figure 8B:
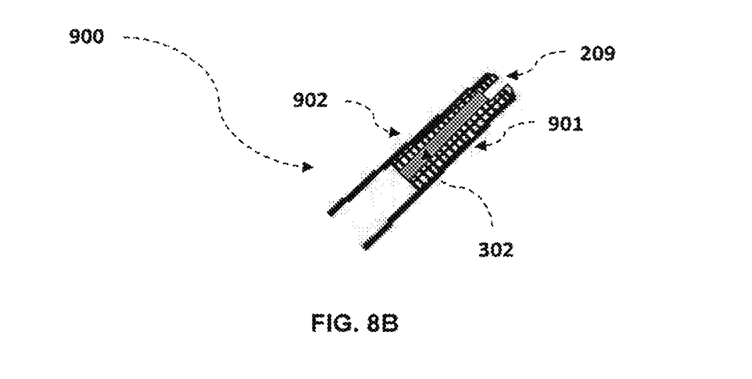
Figure 9A:
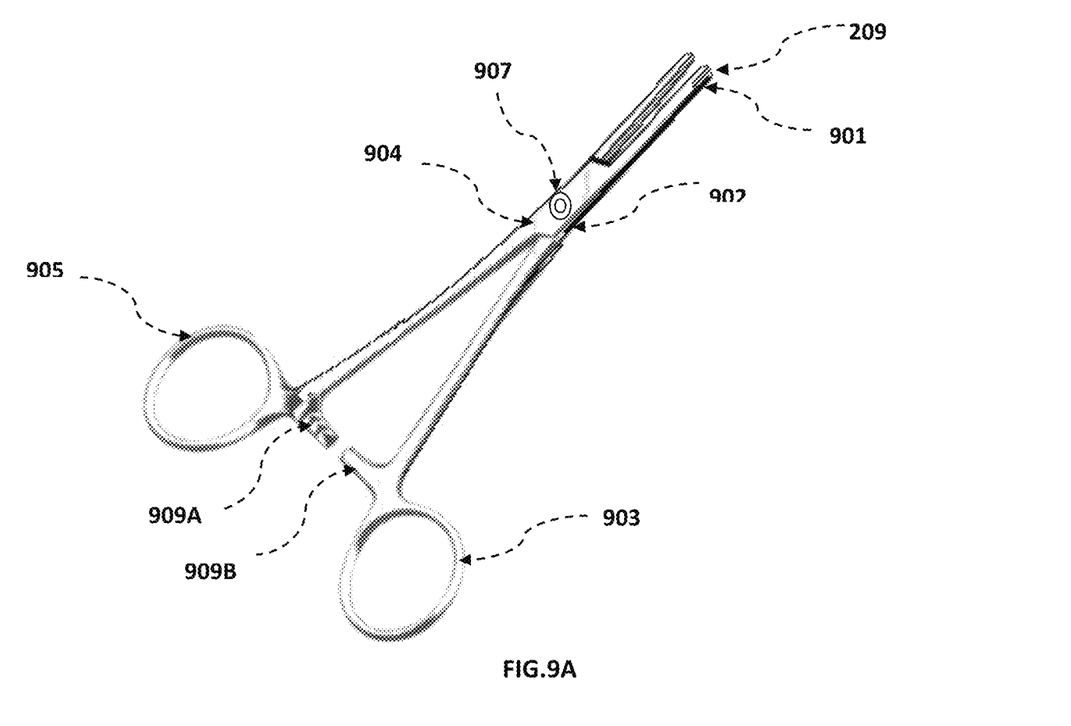
FIGS. 9A-B is perspective view of another shape present invention that is an adjustable gripping type Cartilage of Tissue Holding Forceps constructed in accordance with exemplary embodiments of the present disclosure.
Figure 9B:
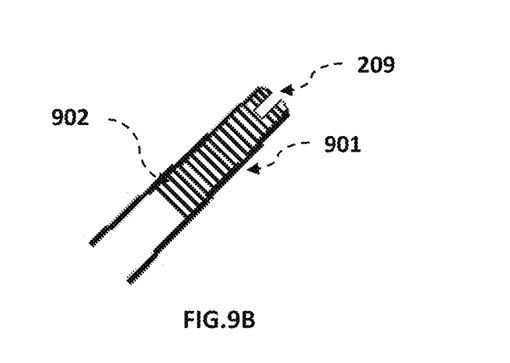

The substitution design for forceps with adjustable clamped for strength of grips is shown in FIGS. 8A-B. Where the novel forceps 900 has novel designed jaw 901 with central cut jaw's tip 209, where 903 and 905 are oval shaped rear ends of the first and the second arms of the novel designed forceps which are connected together at a pivot point 907 by respective midpoints 902 and 904 of the of the first and the second arms, respectively. For the adjustments of strength of grips, the triangle locks or levels 909A and 909B are used which are structurally arranged in opposite direction. For further clear disclosure in FIG. 8B the novel designed jaw 901 with central cut jaw's tip 209 with linear rows of sharp elongated teeth 902 are also shown.

The present disclosed invention includes three major embodiments. First embodiment is the central cut 304 in the jaw tip 209 which can be of various sizes of width and depth. This central cut support in holding the surgical needle during surgical operation and support in the griping skin or tissue. This proper holding of surgical needle during stitching avoids slipping and repeated griping of the needle and accordingly, this save the effort and time of operation.

Second embodiment is the use of variety of teeth like sharp elongated like spines, medium elongated in linear rows and fine but sharp tipped file like teeth. This required teeth shape and size is designed as per requirement of softness of tissue to be handled in the surgery. Third embodiment is the adaptation of feasible shape of the forceps with central cut jaw tip according to the user requirement. This shapes may include but not limit to similar to Adson-Brown tissue forceps, scissor like tungsten Carbide Adson-Brown tissue forceps and electro-Adson-Brown tissue forceps etc.

The novel design can be made by using any tough and hard material including metals and alloys. The making material can be stainless steel, tungsten carbide, titanium, hard plastic or any other stainless metal.

Here some sample scenario of novel designed forceps are described as example cases:

Example No. 1

A novel design of Forceps are constructed by titanium where the shape of the Forceps are like Adson-Brown forceps but with modifications of central cut in the jaw tip of the Forceps where the width of central cut is 0.7 mm and depth is 12 mm from head end towards rear end of each arm of the Forceps. There are two rows of sharp elongated teeth at jaws of each arm of Forceps to support firm grip of tissue which also extends beyond to central cut. There is also a deep groove in the mid of jaw of each arm of the Forceps to support flow of extra waste fluids like blood during operation.

Example No. 2

A novel design of Forceps are constructed by Tungsten Carbide where the shape of the Forceps are like Adson-Brown Tungsten Carbide Forceps but with modifications of central cut in the jaw tip of the Forceps where the width of central cut is 0.6 mm and depth is 10 mm from head end towards rear end of each arm of the Forceps. There are two rows of fine pyramidal shaped sharp teeth somewhat similar to file tool at jaws of each arm of Forceps to support firm grip of tissue which also extends beyond to central cut. There is also a deep groove in the mid of jaw of each arm of the Forceps to support flow of extra waste fluids like blood during operation.

Example No. 3

A novel design of Forceps are constructed by stainless steel where the shape of the Forceps are like adjustable scissor shaped Forceps but with modifications of central cut in the jaw tip of the Forceps where the width of central cut is 0.8 mm and depth is 11 mm from head end towards rear end of each arm of the Forceps. There are four rows of linear fine sharp teeth at jaws of each arm of Forceps to support firm grip of tissue which also extends beyond to central cut. There is also a deep groove in the mid of jaw of each arm of the Forceps to support flow of extra waste fluids like blood during operation.

What is claimed:

1. A tissue holding forceps comprising:—
a first arm of a stainless material with a rear end, and a head end having a jaw and a jaw's tip;
a second arm of a stainless material with a rear end, and a head end having a jaw and a jaw's tip;
the rear end of the first arm is coupled with the rear end of the second arm;
the jaw's tip at the head end of the first arm and the jaw's tip at the head end of the second arm are each centrally cut in deep down from the respective head end towards the respective rear end, thereby making each of the jaw's tips u-shaped, wherein a width size of the cut is between 0.3 mm and 2.0 mm and a linear depth's size is between 3.00 mm and 12.00 mm;
the jaw's tip at the head end of the first arm and the jaw's tip at the head end of the second arm each have at least two linear rows of sharp elongated teeth which are designed in an arrangement such that the teeth on the jaw of the first arm are opposing to the teeth on the jaw of the second arm in an opposite direction, wherein the teeth on the jaw of the first arm are adjusted or interlocked in or between spaces formed between the teeth on the jaw of the second arm when the jaws move towards each other when closing;
the jaw's tip at the head end of the first arm and the jaw's tip at the head end of the second arm each have a deep groove in a center of the rows of the teeth of the respective jaw's tip, the groove having a width less than the width of the cut and extending from a closed end of the respective u-shaped jaw's tip towards the rear end of the respective arm and terminating at a rear-most end of the respective rows of the teeth.

2. The tissue holding forceps as claimed in claim 1, wherein the material of the first arm and the second arm is stainless steel, stainless alloy, titanium, tungsten carbide, hard plastic or a metal.

3. The tissue holding forceps as claimed in claim 1, wherein each tooth of said elongated teeth is pyramidal or elongated or spine like or fine like file tool and triangular in cross-section and terminates in a sharp point, wherein the height of the each tooth is between 0.3 mm and 0.8 mm.

4. The tissue holding forceps as claimed in claim 1, wherein there are at least four linear rows of teeth at the jaws of the first and second arm and at least two columns of opposing teeth on the first and the second jaws in parallel to a length of the forceps first and the second arm.

5. The tissue forceps as claimed in claim 1, wherein each tooth of said elongated teeth on the jaws of the first and the second arm has a base adjacent said respective jaw on which it is located, the height of the each tooth varies being about two to eight times the width of the base of the each tooth.

6. The tissue holding forceps of claim 1 where the rear ends of the forceps are modified to fit in an electric holder and the electric holder is further connected to an electric supply.

7. A tissue holding forceps comprising:
a first arm of a stainless material with an oval shaped rear end with at least two adjustable locks, a midpoint, and a head end having a jaw and a jaw's tip;
a second arm of a stainless material with an oval shaped rear end with at least two adjustable locks, a midpoint, and a head end having a jaw and a jaw's tip;
the midpoint of the first arm is connected with the midpoint of the second arm at a pivot point;
the adjustable locks of the first and the second arms are relatively adjacent when the first and the second arms are connected at the pivot point;
the jaw's tip at the head end of the first arm and the jaw's tip at the head end of the second arm are each centrally cut in deep down from the respective head end towards the respective rear end, thereby making each of the jaw's tips u-shaped, wherein a width size of the cut is between 0.3 mm and 2.0 mm and a linear depth's size is between 3.00 mm and 12.00 mm;
the jaw's tip at the head end of the first arm and the jaw's tip at the head end of the second arm each have at least two linear rows of sharp elongated teeth which are designed in an arrangement such that the teeth on the jaw of the first arm are opposing to the teeth on the jaw of the second arm in an opposite direction, wherein the teeth on the jaw of the first arm are adjusted or interlocked in or between spaces formed between the teeth on the jaw of the second arm when the jaws move towards each other when closing;
the jaw's tip at the head end of the first arm and the jaw's tip at the head end of the second arm each have a deep groove in a center of the rows of the teeth of the respective jaw's tip, the groove having a width less than the width of the cut and extending from a closed end of the respective u-shaped jaw's tip towards the rear end of the respective arm and terminating at a rear-most end of the respective rows of the teeth.

8. The tissue holding forceps as claimed in claim 7, wherein the material of the first arm and the second arm is stainless steel, stainless alloy, titanium, tungsten carbide, hard plastic or a metal.

9. The tissue holding forceps as claimed in claim 7, wherein each tooth of said elongated teeth is pyramidal or elongated or spine like or fine like file tool and triangular in cross-section and terminates in a sharp point, wherein the height of the each tooth is between 0.3 mm and 0.8 mm.

10. The tissue holding forceps as claimed in claim 7, wherein there are at least four linear rows of teeth at the jaws of the first and the second arm and at least two columns of opposing teeth on the first and the second jaws in parallel to a length of the forceps first and the second arm.

* * * * *